United States Patent [19]

Baudy et al.

[11] Patent Number: 5,124,319
[45] Date of Patent: Jun. 23, 1992

[54] BENZIMIDAZOLE PHOSPHONO-AMINO ACIDS

[75] Inventors: Reinhardt B. Baudy, Yardley; Horace Fletcher, III, Pottstown; John P. Yardley, Gulph Mills, all of Pa.

[73] Assignee: American Home Products Corporation, New York, N.Y.

[21] Appl. No.: 776,528

[22] Filed: Oct. 11, 1991

[51] Int. Cl.$^5$ ............... C07D 235/15; A61K 31/415
[52] U.S. Cl. ........................................ 514/80; 548/113
[58] Field of Search .................. 548/113; 514/387, 80

[56] References Cited

U.S. PATENT DOCUMENTS 4,746,653  5/1988  Hutchison et al. ................. 514/89

FOREIGN PATENT DOCUMENTS 959724  5/1981  European Pat. Off. .......... 548/113

*Primary Examiner*—Mary Lee
*Assistant Examiner*—Joseph K. McKane
*Attorney, Agent, or Firm*—George Tarnowski

[57] ABSTRACT

The compounds of the formula

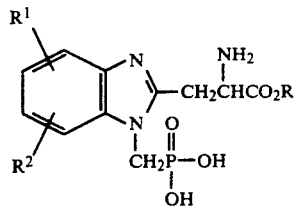

wherein
R is hydrogen, lower alkyl, benzyl or pivaloyloxymethyl;
$R^1$ and $R^2$ are, independently, hydrogen, lower alkyl, lower alkoxy, trifluoromethyl, trifluoromethoxy, methanesulfonylamino, acetylamino, or halo, or when taken together $R^1$ and $R^2$ represent a methylenedioxy grouping;

and the pharmacologically acceptable salts thereof are NMDA antagonists useful in the treatment and prevention of central nervous system related pathological conditions resulting from overstimulation by excitatory amino acids.

7 Claims, No Drawings

BENZIMIDAZOLE PHOSPHONO-AMINO ACIDS

BACKGROUND OF THE INVENTION

L-Glutamate and L-aspartate, the endogenous acidic amino acids, have been firmly established as major excitatory neurotransmitters. The action of these excitatory amino acids is mediated by several distinct receptor subtypes of which the best studied one is the N-methyl-D-aspartate (NMDA) receptor. Excessive activation of the NMDA receptor complex may cause neuronal overstimulation with pathological consequences. Experimental evidence suggests that a prolonged, agonist-evoked conductance of the NMDA-gated ion channel permits an abnormal enhancement of calcium entry, and the resulting increased levels of intracellular calcium play a pivotal, deleterious role in the excitotoxic neuronal damage, neurodegeneration, and delayed neuronal death.

Excitatory amino acids have been implicated in neuropathologies of traumatic, endogenous genetic, and environmental origin. Brain damage associated with anoxia, hypoglycemia, traumatic injury, stroke, epilepsy, specific metabolic defects, and some chronic neurodegenerative diseases is, to a large extent, produced by excitotoxic mechanisms.

A number of studies have demonstrated that a blockade of the NMDA-subclass receptor significantly reduces a neuronal damage and loss which occurs in animal models mimicking a variety of neuropathological situations. These observations strongly indicate that NMDA antagonists offer effective neuroprotection in several clinical settings. Thus, agents antagonizing the excitotoxic effects mediated by the NMDA receptor are beneficial in the treatment of ischemic conditions, stroke, brain or spinal cord injury, and generally, in patients with escalating levels of excitatory transmitters. Specific applications also include therapy of senile dementia Alzheimer-type, parkinsonian dementia complex, Huntington's chorea, and other dominant or recessive spinocerebellar degenerations where NMDA antagonists prevent or retard the progression of the disease.

DESCRIPTION OF THE INVENTION

The compounds of the invention are competitive NMDA antagonists which have the following formula

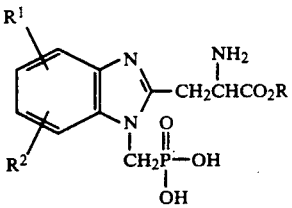

wherein
R is hydrogen, lower alkyl, benzyl or pivaloyloxymethyl;
$R^1$ and $R^2$ are, independently, hydrogen, lower alkyl, lower alkoxy, trifluoromethyl, trifluoromethoxy, methanesulfonylamino, acetylamino, or halo, or when taken together $R^1$ and $R^2$ represent a methylenedioxy grouping;
and the pharmacologically acceptable salts thereof.

The term "lower alkyl" and "lower alkoxy" refer to moieties having 1 to 4 carbon atoms in the carbon chain. The term "halo" refers to fluoro, chloro, bromo and iodo.

The compounds of the invention exhibit chirality and hence the compounds of the invention embrace not only the racemic mixtures but the individual enantiomers as well. The enantiomers are designated according to the R/S-system using the sequence rule.

The compounds of the invention can be prepared by several synthetic routes. According to a preferred scheme, a protected benzimidazolyl-D-alanine precursor is reacted with an alkylphosphonate ester followed by deprotection to yield the desired final products:

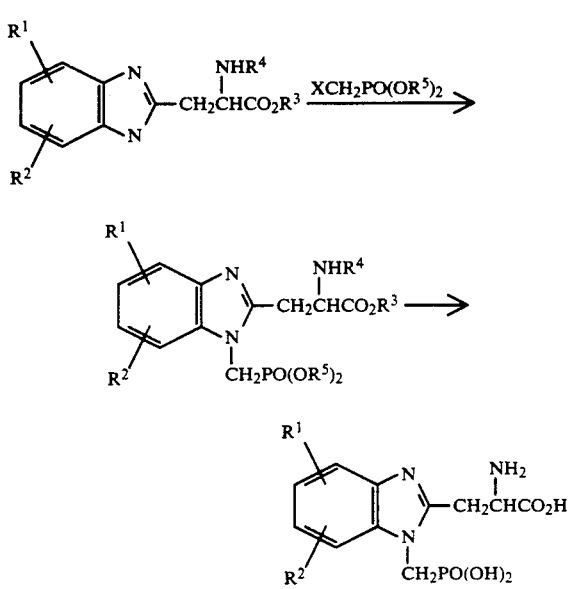

wherein in the above sequence $R^3$ and $R^4$ represent conventional amino acid protecting groups, such as lower alkyl and benzyl for $R^3$ and t-butyloxycarbonyl or benzyloxycarbonyl for $R^4$. The phosphonic acid protecting groups $R^5$ may be lower alkyl, benzyl or 4-nitrobenzyl. The X leaving group of the alkylphosphonic acid reactant may be halo, methylsulfonyl, tolylsulfonyl or trifluorosulfonyl, where trifluorosulfonyl is especially preferred. The protected benzimidazolylalanine precursor can be obtained in optically pure form by an enantioselective synthesis from an R or S, N-protected aspartic acid ester derivative by the method of Nestor et al., *J. Med. Chem.*, 27, 320 (1984). The deprotection of the alkylphosphonylated intermediate can be carried out using acid or basic hydrolysis, hydrogenolysis, and/or trimethylsilylbromide treatment, depending upon the protecting group to be removed. These steps can be permuted or combined, as necessary and suitable. When $R^3$ is benzyl, $R^4$ is benzyloxycarbonyl and $R^5$ is 4-nitrobenzyl, a one-step total hydrogenolytic deprotection can be carried out.

In an alternative sequence, o-phenylenediamine can be reacted with the alkylphosphonate ester reactant to yield a diamino intermediate which is then further reacted according to the method of Nestor et al. cited, supra, to yield a protected intermediate which is then subjected to deprotection as outlined above:

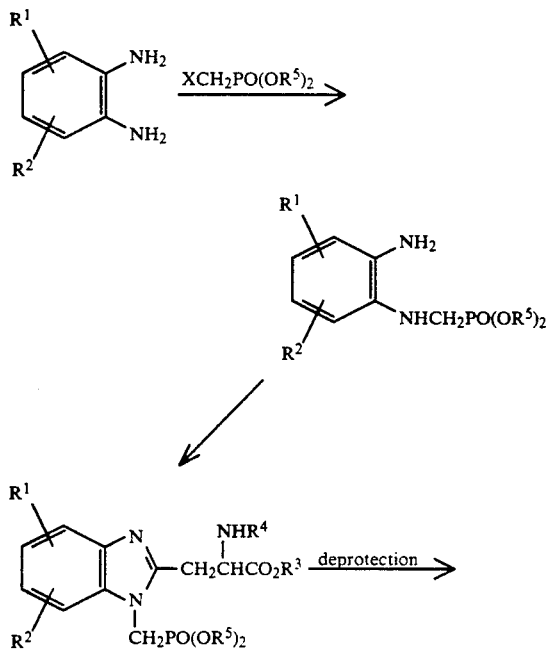

In those cases where the substitution pattern for $R^1$ and $R^2$ on the benzimidazole ring is asymmetrical, whereby alkylation with the alkylphosphonate ester reactant in the above reaction sequences would yield a diasteriometic mixture of products, fractional crystallization or chromatography would be necessary to separate the products. This can be avoided by the use of appropriate starting materials which yield the desired precursor materials. Thus, an appropriately substituted o-nitroaniline or o-halonitrobenzene is reacted with an alkylphosphonate ester reactant or amino-phosphonate ester reactant, respectively, to yield the appropriate intermediate, which is then further reacted by the method of Nestor et al. followed by deprotection to give the desired final products:

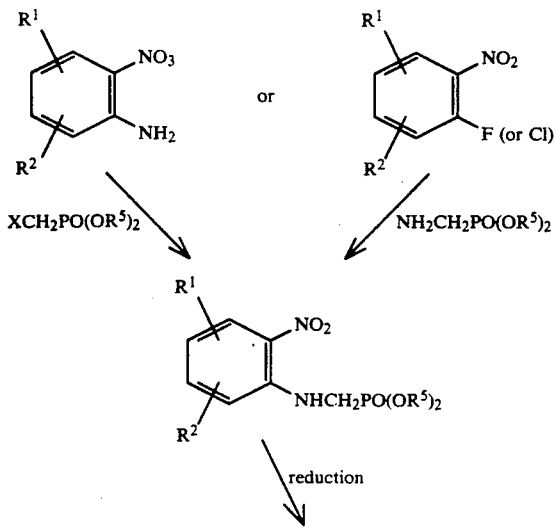

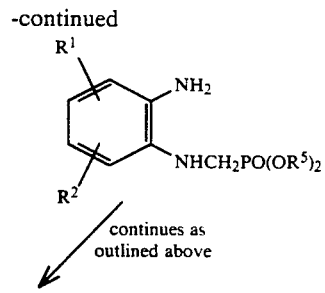

The starting materials in the above sequences are all either commercially available or can be prepared by conventional methods known and reported in the chemical literature.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds of the invention as phosphono-carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of this invention are competitive NMDA antagonists useful in the treatment of convulsions, cerebral ischemias, stroke, brain or spinal cord injury, CNS disorders such as senile dementia, Alzheimer's disease, Huntington's chorea, and other dominant or recessive spinocerebellar degenerations. The said compounds may be especially useful as pre-anesthetics and neuroprotective agents during a high risk surgery, such as brain surgery and spinal cord surgery or as a result of trauma, where the risk of cardiac or pulmonary arrest may cause partial, temporary or complete loss of blood flow to the brain. Additional advantages in the use of the compounds of this invention as pre-anesthetics resides in their mild anxiolytic/sedative properties, their short term memory impairment property (short-term amnesia) and in their ability to potentiate the affect of anesthetics so that the latter may be employed at a lower dose.

Hence, there is herewith provided in addition to the novel compounds, supra, a method for preventing disorders induced by overstimulation of excitatory amino acid receptors in brain and spinal cord which comprises administering to a mammal suffering from such disease states, an NMDA antagonist of the formula presented, supra.

As such, the compounds of this invention may be administered neat or with a pharmaceutical carrier and so they can be formulated into oral dosage forms such as tablets, capsules and the like. The compounds can be administered by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times thoughout the day.

The NMDA competitive antagonist activity of the compounds of the invention may be demonstrated by standard pharmacological procedures which illustrate their in vitro inhibition of [$^3$H]CCP binding in rat brain tissue and their in vivo antagonism of NMDA induced convulsions in mice.

The following examples show the preparation and pharmacological testing of compounds within the invention.

EXAMPLES

Enantiomeric purity of the examples of the invention is determined by a modification of the method of Tapuh, Y., Miller, N., Karger, B. L., *Journal of Chromatography* 1981, 205, 325–337.

Preparation of trifluoromethanesulfonic acid [bis-(4-nitrophenylmethoxy)phosphinyl]methyl ester A solution of di-4-nitrobenzyl hydroxymethylphosphonate (3.82 g, 10.0 mmol) [Hoffmann, M. *Synthesis* 1988 62.] and pyridine (0.87 g, 11.0 mmol) in dichloromethane (50 mL) is treated at −10° C. to −20° C. with trifluoromethanesulfonic anhydride (3.1 g, 11.0 mmol) and stirred at −10° C. for 1 hour. The solution is washed with cold 1N HCl (2×50 mL), cold water (3×50 mL), and dried over MgSO$_4$. The solution is filtered, the solvent is evaporated, and the residual oil solidifies on standing. Yield 4.18 g (80%). The material is sufficiently pure to be used for further reactions. An analytical sample is obtained by dry column chromatography on Grade II–III silica gel with ethyl acetate as eluant. The product fractions are evaporated and the residue crystallized from dichloromethane/hexane and dried: mp 73°–75° C.; $^1$H NMR (400 MHz, CDCl$_3$): δ 8.2 (d, 4H), 7.5 (d, 4H), 5.2 (m, 4H), 4,8 (d, 2H); MS (+FAB) 515 (M+H)+

| Elemental analysis for C$_{16}$H$_{14}$N$_2$O$_{10}$PSF$_3$ | |
|---|---|
| Calc'd: | C, 37.36; H, 2.74; N, 5.45 |
| Found: | C. 37.27; H, 3.03; N, 5.52. |

EXAMPLE 1

R-α-Amino-1-(phosphonomethyl)-1H-benzimidazole-2-propanoic acid, dihydrochloride, dihydrate Benzyl N-(benzyloxycarbonyl)-3-(2-benzimidazoyl)-D-alaninate (30 g, 0.07 mol) (prepared according to the method of Nestor et al., *J. Med. Chem.*, 1984, 27, 320), trifluoromethanesulfonic acid [diethoxyphosphinyl]-methyl ester (23.04 g, 0.076 mol) and powered anhydrous potassium carbonate (37 g, 0.268 mol) are stirred in acetonitrile (500 mL) at room temperature for 20 hours. The mixture is filtered, the filtrate evaporated and the residue dissolved in dichloromethane. The dichloromethane is washed with water (500 mL), 5% NaHCO$_3$ (2×300 mL), water (300 mL), and dried over MgSO$_4$. The solution is filtered and the solvent evaporated to a gum. Yield 43 g. The gum is dissolved in dichloromethane (300 mL) and purified by chromatography on dry column silica gel with a gradient elution (methylene chloride to ethyl acetate). The product fractions [R$_f$ (methylene chloride/ethyl acetate 4:1) 0.17] are pooled and evaporated to a gum. Yield 10.6 g (26%). $^1$H NMR (400 MHz, CDCl$_3$): δ 7.7 (d, 1H), 7.35 (s, 5H), 7.3 (s, 5H), 7.2 (s, 2H), 6.9 (d, 1H), 5.2–5.0 (m, 5H), 4.4–4.2 (m, 2H), 4.1 (m, 1H), 3.9 (m, 4H), 3.6 (dd, 1H), 3.4 (dd, 1H), 1.2 (t, 3H), 1.1 (t, 3H); MS (+FAB) 580 (M+H)+. The material (10.6 g, 0.0183 mol) is dissolved in acetic acid (300 mL) and shaken with 10% Pd/C (1 g) under 1 atm. of H$_2$ at room temperature until H$_2$ uptake ceases, the filtrate is evaporated and the residue co-evaported with dioxane (4×100 mL). IR, NMR, and Mass Spectra of the residue (8 g) shows removal of the benzyl protecting groups. 7.5 g of the residue and trimethylsilyl bromide (15 g, 0.1 mol) are refluxed under N$_2$ in dichloroethane (110 mL) for 1.5 hours. Solvent is evaporated and the residue is stirred in water (50 mL) and ether (50 mL). A solid forms which is filtered and retained. The filtrate is separated, the aqueous layer diluted with ethanol (50 mL) and treated with propylene oxide (10 mL) with stirring for 0.5 hours. The solution is evaporated to remove ethanol and the solid which forms is combined with the solid obtained earlier. The product is dissolved in 1N HCl (100 mL) and the filtered solution evaporated to dryness. Yield of 4 g (65%) based on fully protected intermediate. The product is crystallized from warm water (50 mL) and ethanol (100 mL) and dried in vacuo. Yield 2.27 g (37%). The compound did not melt below 310° C. $^1$H NMR (400 MHz, DMSO-d$_6$): δ 7.5 (t, 2H), 7.3 (m, 2H), 4.35 (d, 2H), 4.25 (t, 1H), 3.5 (m, 2H); MS (-FAB) 298 (M-H)-;.[a]$_D^{25}$=−49.5° (c=1.01 1N HCl); HPLC analysis: enantiomeric purity: 1S:99R.

| Elemental analysis for C$_{11}$H$_{14}$N$_3$O$_5$P.2 H$_2$O: | |
|---|---|
| Calc'd: | C, 38.88; H, 5.41; N, 12.37 |
| Found: | C, 38.95; H, 5.13; N, 12.52. |

The dihydrochloride dihydrate is prepared by dissolving the free acid in 2N HCl, evaporating to dryness and drying in vacuo. $^1$H NMR (400 MHz, DMSO-d$_6$): δ

9.2–8.2 (m, 2H), 7.9 (d, 1H), 7.7 (d, 1H), 7.5 (m, 2H), 4.8 (m, 3H), 3.8 (d, 2H); $[a]_D^{25} = -41.6°$ (c = 1.0, 1N HCl).

| Elemental analysis for $C_{11}H_{14}N_3O_5P \cdot 2\, HCl \cdot 2\, H_2O$: | |
|---|---|
| Calc'd: | C, 32.37; H, 4.93; N, 10.29 |
| Found: | C, 32.57; H, 4.87; N, 10.53. |

EXAMPLE 2

R-α-Amino-5,6-dichloro-1-(phosphonomethyl)-1H-benzimidazole-2-propanoic acid, dihydrochloride In a manner similar to Example 1, but using benzyl N-(benzyloxycarbonyl)-3-[(5,6-dichloro)-2-benzimidazoyl]-D-alaninate (prepared according to the method of Nestor et al., *J. Med. Chem.*, 1984, 27, 320), the title compound is prepared (Yield 15.3%). m.p. indefinite. $^1$H NMR (400 MHz, DMSO-d$_6$): δ 8.55 (s, 3H), 8.95 (s, 1H), 8.85 (s, 1H), 4.6 (d, 2H), 4.55 (t, 1H), 3.8 (m, 2H); MS (-FAB) 366 (M-H)$^-$; $[a]_D^{25} = -50.0°$ (c = 1.01; 1N HCl); HPLC analysis (free acid) enantiomeric purity: 2.6S:97.4R

| Elemental analysis for $C_{11}H_{12}N_3O_5PCl_2 \cdot 2\, HCl$: | |
|---|---|
| Calc'd: | C, 29.96; H, 3.20; N, 9.53 |
| Found: | C, 29.78; H, 3.31; N, 9.65. |

EXAMPLE 3

R-α-Amino-5,6-dimethyl-1-(phosphonomethyl)-1H-benzimidazole-2-propanoic acid, dihydrochloride Benzyl N-(benzyloxycarbonyl)-3-[(5,6-dimethyl)-2-benzimidazoyl]-D-alaninate (see Nestor et al., *J. Med. Chem.*, 1984, 27, 320) (3.7 g, 0.8 mmol), trifluoromethanesulfonic acid [bis-(4-nitrophenylmethoxy)phosphinyl]methyl ester (5.5 g, 10 mmol), and powdered anhydrous K$_2$CO$_3$ (5.5 g, 40 mmol) are stirred in acetonitrile (100 mL) at room temperature under N$_2$ (20 h). The acetonitrile is evaporated and the residue is shaken with dichloromethane (100 mL) and H$_2$O (2 × 100 mL). The dichloromethane layer is washed with 5% NaHCO$_3$ (2 × 100 mL), brine (100 mL), and dried over MgSO$_4$. The filtered solution is evaporated and the residual gum is dissolved in acetic acid (100 mL) and shaken on a Parr hydrogenation apparatus with 10% Pd/C (1 g) and H$_2$ (38 p.s.i. initial) until H$_2$ uptake ceases (3 h). The filtered solution is evaporated and coevaporated with dioxane (3 × 50 mL), and the residue diluted with water (50 mL). The mixture is adjusted to pH3 with 6N HCl, chilled, and filtered. The air dried solid (2.8 g) is dissolved in water (50 mL) with 1N HCl (1 mL) and reprecipitated by adding 1N NaOH (1 mL). The product is washed with water, ethanol, and ether. IR, NMR, and Mass spectra are consistent for the phosphonomethyl amino acid. The material is dissolved in 1N HCl (20 mL), treated with activated carbon and chilled. The dihydrochloride salt is filtered, washed with ice water and dried in vacuo. Yield 1.23 g (37.4%). $^1$H NMR (400 MHz, DMSO-d$_6$+20% DCl/D$_2$O (2 drops)): δ 7.75 (s, 1H), 5.7 (s, 1H), 5–4.75 (m, 3H), 3.85 (m, 1H), 2.35 (s, 3H); MS (-FAB) 326 (M-H)$^-$; $[a]_D^{25} = -54.4°$ (c = 1.01, 1N HCl); HPLC analysis: enantiomeric purity: 1S:99R.

| Elemental analysis for $C_{13}H_{18}N_3O_5P \cdot 2\, HCl$ | |
|---|---|
| Calc'd: | C, 39.02; H, 5.04; N, 10.50 |
| Found: | C, 38.62; H, 5.27; N, 10.32. |

EXAMPLE 4

R-(-)-α-Amino-1-(phosphonomethyl)-1H-benzimidazole-2-propanoic acid, dihydrochloride, monohydrate Following the procedure of Example 3 and using benzyl-N-(benzyloxycarbonyl)-3-(2-benzimidazoyl)-D-alaninate, the title compound is prepared. Crystallization from hot water and prolonged drying in vacuo results in a hydrate with 3.5 moles of water, yield (61%). $^1$H NMR (400 Hz, DMSO-d$_6$+DCl): δ 7.95 (q, 1H), 7.8 (q, 1H), 7.55 (2H), 4.8 (m, 3H), 3.8 (d, 2H); $[a]_D^{25} = 53.1°$ (c = 1.03 1N HCl); HPLC analysis enantiomeric purity: 1.3S: 98.7R.

| Elemental analysis for $C_{11}H_{14}N_3O_5P \cdot 3.5\, H_2O$ | |
|---|---|
| Calc'd: | C, 36.46; H, 5.84; N, 11.59 |
| Found: | C, 36.67; H, 5.64; N, 11.74. |

The dihydrochloride is prepared by dissolving in 2N HCl (5 mL) and water (15 mL) and evaporating to dryness. $[a]_D^{25} = -40.2°$ (c = 1.0, 1N HCl).

| Elemental analysis for $C_{11}H_{14}N_3O_5P \cdot 2\, HCl \cdot H_2O$ | |
|---|---|
| Calc'd: | C, 33.86; H, 4.65; N, 10.77 |
| Found: | C, 33.77; H, 4.59; N, 10.67. |

EXAMPLE 5

R-α-Amino-1-(phosphonomethyl)-1H-benzimidazole-2-propanoic acid, 2-amino-2-(hydroxymethyl)-1,3-propanediol (1:2). trihydrate The free acid compound of Example 4 (1.86 g, 5 mmol) and tromethamine base (1.33 g, 11 mmol) are warmed in water (10 mL) and precipitated with ethanol (100 mL). The material is filtered, washed with ethanol, then ether and air dried overnight. The product is recrystallized from warm water (30 mL) and ethanol (200 mL), filtered, washed with ethanol and dried in vacuo over P$_2$O$_5$. Yield 2.58 g (86.6%).

| Elemental analysis for $C_{11}H_{14}N_3O_5P \cdot 2\, C_4H_{11}NO_3 \cdot 3\, H_2O$ | |
|---|---|
| Calc'd: | C, 38.35; H, 7.11; N, 11.77 |
| Found: | C, 38.39; H, 6.76; N, 11.86. |

EXAMPLE 6

S-α-Amino-1-(phosphonomethyl)-1H-benzimidazole-2-propanoic acid, dihydrochloride, hydrate Benzyl N-(benzyloxycarbonyl)-3-(2-benzimidazoyl)-L-alaninate (2.85 g, 6.3 mmol), trifluoromethanesulfonic acid [bis-(4-nitrophenylmethoxy)phosphinyl]methyl ester (3.67 g, 8.9 mmol), and powdered anhydrous potassium carbonate (4 g, 28.9 mmol) are stirred in acetonitrile (100 mL) at room temperature overnight. Thereafter, the procedure of Example 1 is continued and a tetrabenzyl derivatives obtained. The crude product (4.3 g) is purified on a Waters prep 500 HPLC using gradient elution of hexane (100%) to ethyl acetate (100%). Yield 1.0 g. The product is dissolved in acetic acid with 10% Pd/C (0.5 g) and hydrogenated at 1 atm. The mixture is filtered, evaporated on a Rotovapor, flushed with dioxane twice and stirred in water (10 mL). The product is filtered and dried. Yield 0.35 g (17.6%); NMR identical to product from Example 1 MS(+FAB) 300 (M+H)+[a]$_D^{25}$= +32.8° (c=1.45, methanol +HCl); HPLC analysis enantiomeric purity: 98.2S/1.8R.

| Elemental analysis for $C_{11}H_{14}N_3O_5P.H_2O$ | |
| --- | --- |
| Calc'd: | C, 41.65; H, 5.08; N, 13.25 |
| Found: | C, 41.60; H, 5.04; N, 13.09. |

EXAMPLE 7

R-α-Amino-6-chloro-1-(phosphonomethyl)-1H-benzimidazole-2-propanoic acid, 0.8 hydrochloride, hydrate A) Under dry nitrogen N-Boc-D-aspartic acid α-benzyl ester (13.4 mmole, 4.34 g) is dissolved in dry tetrahydrofuran (67 mL) and cooled to −10° C. In succession, triethylamine (13.4 mmole, 1.86 mL) and ethyl chloroformate (13.4 mmole, 1.28 mL) are added and the reaction mixture stirred for 10 minutes at −10° C. after which a solution of commercial 4-chloro-1,2-phenylenediamine (14.7 mmole, 2.1 g) in dry tetrahydrofuran (27 mL) is added slowly. The mixture is allowed to warm slowly to ambient temperature. It is then poured into ice cold brine (150 mL), extracted with ethyl acetate (2×100 mL). The combined organic layer is washed successively with ice cold saturated NaHCO$_3$ (100 mL), then brine (100 mL) and then dried over MgSO$_4$, filtered, and evaporated to dryness in vacuo. The residue is chromatographed (HPLC). Elution with ethyl acetate/hexane gives 2.9 g N$^4$-(2-amino-5-chlorophenyl)-N$^2$-[(dimethylethoxy)carbonyl]-D-asparagine phenylmethyl ester.

B) A solution of the above oil (4.8 mmole, 2.15 g) in glacial acetic acid (70 mL) is heated to 70° C. for 5 hours under exclusion of moisture is then evaporated in vacuo and the residue flash chromatographed on silica gel (60 g). Elution with 20% ethyl acetate/hexane affords 1.6 g 6-chloro-α[(1,1-Dimethylethoxy)carbonyl]amino]-1H-benzimidazole-2-propanoic acid phenylmethyl ester as an oil.

C) A solution of the oil of Step B (3.7 mmole, 1.6 g) in acetonitrile (50 mL) is treated at 25° C. under dry nitrogen with trifluoromethanesulfonic acid [dimethoxyphosphinyl]methyl ester (4.1 mmole, 1.115 g) and anhydrous powdered potassium carbonate (10 mmole, 1.38 g). The reaction mixture is stirred at 25° C. overnight, filtered, washed with methylene chloride (20 mL), the combined filtrate evaporated in vacuo and the residue partitioned between methylene chloride-water. The organic layer is separated, dried over MgSO$_4$, filtered, and evaporated in vacuo. The residue is flash chromatographed on silica gel (60 g). Elution with chloroform/ethyl acetate affords 1.4 g. 6-chloro-1-[(dimethoxyphosphinyl)methyl]-α-[[(1,1-dimethylethoxy)carbonyl]amino]-1H-benzimidazole-2-propanoic acid phenylmethyl ester as an oil.

D) A solution of the oil of Step C (2.5 mmole, 1.4 g) in glacial acetic acid (20 mL) is treated with 10% palladium on charcoal (140 mg) and hydrogenated for ∼3 hours at 25° C. The reaction mixture is purged with nitrogen, filtered through Solka-floc, the cake washed with acetic acid (10 mL) and the filtrate evaporated to dryness in vacuo. The residue is stripped with toluene (2×10 mL) and evaporated in high vacuo to afford 1.15 g 6-chloro-1-[(dimethoxyphosphinyl)methyl]-α[[1,1-dimethylethoxy)carbonyl]amino]]-1H-benzimidazole-2-propanoic acid as an oil.

E) The oil of Step D (1.9 mmole, 0.9 g) is refluxed in 6N HCl (20 mL) for 45 minutes. The reaction mixture is then evaporated to dryness in vacuo, the residue stripped with toluene (2×20 mL) and then crystallized from hot water/acetonitrile to afford 330 mg of the title compound; mp 198°–200° C. $^1$H NMR (DMSO-d$_6$=1 drop DCl, 400 MHz): δ 3.87 (dd, J$_1$=5.5 Hz, J$_2$=7.2 Hz, 2H, CH-CH$_2$), 4.86 (t, J=7.2 Hz, 1H, CH-CH$_2$), 4.96 (dd, J$_1$=12 Hz, J$_2$=32.7 Hz, 2H, CH$_2$-P), 7.59 (dd, J$_O$=8.7 Hz, J$_m$=2 Hz, 1H, H-5), 7.83 (d, J$_O$=8.8 Hz, 1H, H-4), 8.13 (d, J$_m$=1.9 Hz, 1H, H-7).

| Elemental analysis for $C_{11}H_{13}ClN_3O_5P.0.8\ HCl.H_2O$ | |
| --- | --- |
| Calc'd: | C, 36.62; H, 4.47; N, 11.64 |
| Found: | C, 36.32; H, 4.55; N, 11.35. |

EXAMPLE 8

R-α-Amino-5-chloro-1-(phosphonomethyl)-1H-benzimidazole-2-propanoic acid hydrochloride A) Procedure as in Example 7A), however, the residue obtained is not purified, but rather used as is in the next step.

B) Procedure as in Example 7B), however, the residue obtained is not purified, but rather used as is in the next step.

C) The oil obtained from Step B (21.8 mmole, 9.4 g, mixture of 5-, and 6-chloroegioisomers) in acetonitrile (250 mL) is treated at once under dry nitrogen and stirring with trifluoromethanesulfonic acid [dimethoxyphosphinyl]methyl ester (24 mmole, 6.528 g) and anhydrous, powdered K$_2$CO$_3$ (65 mmole, 8.97 g). The reaction mixture is stirred at 25° C. overnight, filtered and washed with acetonitrile. The filtrate is evaporated and the residue partitioned between water-methylene chloride. The separated organic layer is dried, and then evaporated in vacuo to dryness. The residue is chromatographed (HPLC), elution with ethyl acetate-hexane giving 4 g. 5-chloro-1-[(dimethoxyphosphinyl)methyl]-alpha-[[(1,1-dimethylethoxy)carbonyl]amino]-1H-benzimidazole-2-propanoic acid phenylmethyl ester as an oil.

D) A solution of the oil of Step C (7.25 mmole, 4 g) in glacial acetic acid (60 mL) is treated with 10% palladium (charcoal(400 mg) and hydrogenated at 25° C. at atmosphere pressure for 4 hours. The mixture is then purged with nitrogen, filtered through Solka-floc, washed with acetic acid (20 mL) and the filtrate evaporated to dryness in vacuo. The residue is stripped with toluene (2×20 mL) and finally evaporated in high vacuo to yield 3.43 g 5-chloro-1-[(dimethoxyphosphinyl)methyl]-α-[[(1,1-dimethylethoxy)carbonyl]amino]-1H-benzimidazole-2-propanoic acid as an oil.

E) The oil of Step D (7.2 mmole, 3.43 g) is refluxed in 6N hydrochloric acid (60 mL) for 50 minutes. The mixture is then evaporated to dryness in vacuo, and the residue once more evaporated with water (15 mL). The residue is dried in high vacuo, and then crystallized from hot water/acetonitrile. The compound is filtered, washed with ether (10 mL) and dried at 1 Torr, 60° C. (over $P_2O_5$) to yield 1.4 g of the desired product; mp 113°-6° C. (Decomp.). $^1$H NMR (DMSO-$d_6$+1 drop DCl, 400 MHz): δ 3.86 (t, J=6.4 Hz, 2H, CH-CH$_2$), 4.83 (t, J=6.8 Hz, 1H, CH-CH$_2$), 4.95 (m, 2H, CH$_2$-P), 7.61 (dd, J$_0$ =8.9 Hz, J$_m$=1.9 Hz, 1H, H-6), 7.91 (d, J$_m$=1.7 Hz, 1H, H-4), 7.96 (d, J$_0$ =8.9 Hz, 1H,H-7).

| Elemental analysis for $C_{11}H_{13}ClN_3O_5P\cdot HCl$ | |
| --- | --- |
| Calc'd: | C, 35.69; H, 3.81; N, 11.35 |
| Found: | C, 35.87; H, 3.94; N, 11.26. |

EXAMPLE 9

S-α-Amino-5,6-dichloro-1-(phosphonomethyl)-1H-benzimidazole-2-propanoic acid, dihydrate The compound is prepared according to the procedure of Example 7; mp 230 (Decomp.). $^1$H NMR (DMSO-$d_6$+drop DCl): δ 3.78 (d, J=7 Hz, 2H, CH$_2$-CH), 4.72 (t, J=7 Hz, 1H, CH-CH$_2$), 4.86 (m, 2H, CH$_2$-P), 8.06 (s, 1H, Ar-H), 8.23 (s, 1H, Ar-H); MS: (-FAB) m/e: 366 (M-H); $[a]_D^{25}$+58.8° (1N HCl):

| Elemental analysis for $C_{11}H_{12}Cl_2N_3O_5P\cdot 2\,H_2O$ | |
| --- | --- |
| Calc'd: | C, 32.69; H, 3.99; N, 10.39 |
| Found: | C, 32.66; H, 4.13; N, 10.34. |

EXAMPLE 10

The compounds of the invention are tested for their NMDA competitive antagonist activity by their ability to displace tritiated 3-(2-carboxypiperazine-4-yl)propyl-1-phosphonic acid (CPP), a known competitive NMDA antagonist, in rat frontal cortex homogenates in the in vitro [$^3$H]CPP binding assay.

This assay is carried out as follows:

Rats are decapitated and their brains are immediately removed, weighed and placed in approximately 15 volumes of ice cold 10% sucrose. Each brain is homogenized using a Potter Elvehjem glass homogenizer (12 strokes at 840 rpm) equipped with a Teflon pestle. The homogenate is then centrifuged at 1,000×g. for 10 minutes. The resulting pellet is discarded and the supernatant is centrifuged at 20,000×g. for 20 minutes. The crude mitochondrial pellet is resuspended in ice cold distilled water and dispersed using a Brinkmann Polytron (PT-10 at setting of 6 for 30 seconds). The suspension is centrifuged at 8,000×g. for 20 minutes. The resulting supernatant and buffy coat is centrifuged at 48,000×g. for 20 minutes. The final crude synaptic membrane pellet is resuspended in ice cold distilled water and centrifuged at 48,000×g. for 20 minutes.

To facilitate removal of endogenous glutamate, the membranes are resuspended in 15 volumes of ice cold 50 mMolar TRIS (pH 7.6) containing 0.04% Triton X-100. The suspension is incubated at 37° C. for 15 minutes, and then centrifuged at 20,000×g. for 20 minutes. The pellet is washed (i.e., resuspended in ice cold TRIS buffer and centrifuged at 20,000×g. for 20 minutes) twice. The membrane pellet is finally resuspended in 15 volumes ice cold 50 mMolar TRIS, distributed to several centrifuge tubes and centrifuged at 20,000×g. for 20 minutes and the pellets are frozen (−70° C.) for subsequent use in binding assays.

For the binding assay, the membrane pellets are thawed and resuspended in 15 volumes ice cold 50 mMolar TRIS (pH 7.6) buffer. Triplicate samples (1000 μl) of the membrane suspension containing between 0.2 and 0.4 mg protein/ml are incubated at 23° C. for 15 minutes with 8 nM [$^3$H]CPP (New England Nuclear), one of various test solutions, and buffer in a final incubation volume of 2 ml using plastic minivials (Skatron). The samples are then centrifuged at 48,000×g. for 20 minutes and the supernatants discarded. The pellets are digested with tissue solubilizer (NCS, Amersham; 500 μl/sample) for 1 hour. Hydrochloric acid (100 μl of 4N) is added to each sample to reduce chemiluminescence during subsequent counting. Scintillation cocktail (Aqasol, DuPont; 3.2 ml) is added to each of the minivials which are then capped and shaken for 15 minutes prior to counting. The vials are placed into a Packard 460 CD (or equivalent) counter for determination of radioactivity.

Total specific binding is defined as total binding less the binding in the presence of 1 mMolar NMDA. Specific binding in the presence of a test drug is expressed as a percent of total specific binding when no drug is present. When test compounds are examined for a dose-response relationship, the results are then plotted as the logit of % binding vs. the log of the test drug concentration. Linear regression analysis then yields a straight line from which an IC$_{50}$ with 95% confidence limits can be calculated.

| STANDARD COMPOUNDS: | |
| --- | --- |
| Ligand | IC$_{50}$ ± S.E., M.(mM), (μ) |
| L. Glutamic Acid | 64.3 ± 4.7, 3 |
| AP7 | 639.2 ± 128.6, 3 |
| NMDA | 1,882.6 ± 612.2, 5 |

When tested in this assay, the compounds of the invention gave the following results.

| Compound of Example No. | IC$_{50}$, nM |
| --- | --- |
| 1 | 59 |
| 2 | 18.2 |
| 3 | 123 |
| 6 | 63% at 10 μM |
| 7 | 21.7 |
| 8 | 7 |
| 9 | 1010 |

EXAMPLE 11

The compounds of the invention are further tested for their in vivo ability to antagonize NMDA in the murine NMDA-induced convulsion assay.

This assay is carried out as follows:

Male Swiss-albino mice (CD-1 strain, Charles River) 18-22 grams in weight, after 18 hours of food deprivation, are habituated to an observation chamber for 30 minutes. The mice are pretreated with the representative test compound followed thirty minutes later with NMDA, 195 mg/kg, i.p., which is a dose normally causing 90% mortality resulting from motor seizures including uncontrollable hind leg scratching or limbs and/or torso muscle jerking with loss of righting reflex followed by death within the 30 minute observation period after NMDA administration. From the latter, the ED$_{50}$ for survival is determined.

Data analyzed using the probit analysis program PS-NONLIN (Natural Response Rate Version). The output of this program contains the statistical significance of the slope of the dose-response and the ED 50% and 95% confidence limits for survival.

| Compound | Reference Compounds: | |
|---|---|---|
| | ED$_{50}$% mg/kg, i.p.* | 95% Confidence Interval for Survival |
| Diazepam | 1.91 | .65–5.62 |
| CPP | 1.04 | .59–1.84 |
| MK-801 | 0.19 | .14–.25 |

*All reported values fit the probit model, (using Pearson Chi Square), and have a significant dose response (slope significant at 0 < 0.05, two tailed test). Compounds having activity in this test procedure are generally recognized in the scientific literature as having broad anti-convulsant utility.

When tested in this assay, the compounds of the invention gave the following results:

| Compound of Example No. | ED$_{50}$, mg/kg, i.p. or % survival |
|---|---|
| 1 | 2.0 |
| 2 | 2.7 |
| 3 | 10% at 3 mg/kg |
| 7 | <5 |
| 8 | 0.13 |
| 9 | >10 |

What is claimed is:

1. A compound having the formula

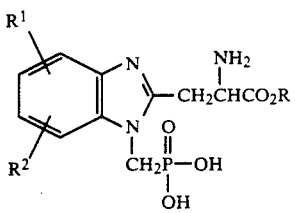

wherein
R is hydrogen, lower alkyl, benzyl or pivaloyloxymethyl;
R$^1$ and R$^2$ are, independently, hydrogen, lower alkyl, lower alkoxy, trifluoromethyl, trifluoromethoxy, methanesulfonylamino, acetylamino, or halo, or when taken together R$^1$ and R$^2$ represent a methylenedioxy grouping;
and the pharmacologically acceptable salts thereof.

2. The compound of claim 1, having the name R-α-amino-1-(phosphonomethyl)-1H-benzimidazole-2-propanoic acid.

3. The compound of claim 1, having the name R-α-amino-5,6-dichloro-1-(phosphonomethyl)-1H-benzimidazole-2-propanoic acid.

4. The compound of claim 1, having the name R-α-amino-5,6-dimethyl-1-(phosphonomethyl)-1H-benzimidazole-2-propanoic acid.

5. The compound of claim 1, having the name R-α-amino-6-chloro-1-(phosphonomethyl)-1H-benzimidazole-2-propanoic acid.

6. The compound of claim 1, having the name R-α-amino-5-chloro-1-(phosphonomethyl)-1H-benzimidazole-2-propanoic acid.

7. A method for the treatment of neuropathological disorders induced by overstimulation of excitatory amino acid receptors which comprises administering to a mammal suffering from such disorders a neuroprotective amount of an NMDA antagonist of the formula:

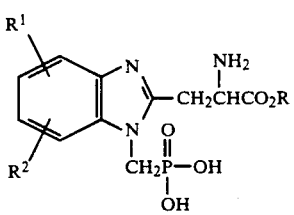

wherein
R is hydrogen, lower alkyl, benzyl or pivaloyloxymethyl;
R$^1$ and R$^2$ are, independently, hydrogen, lower alkyl, lower alkoxy, trifluoromethyl, trifluoromethoxy, methanesulfonylamino, acetylamino, or halo, or when taken together R$^1$ and R$^2$ represent a methylenedioxy grouping;
and the pharmacologically acceptable salts thereof.

* * * * *